United States Patent [19]
Honjo et al.

[11] Patent Number: 5,525,486
[45] Date of Patent: Jun. 11, 1996

[54] PROCESS FOR CONSTRUCTING CDNA LIBRARY, AND NOVEL POLYPEPTIDE AND DNA CODING FOR THE SAME

[75] Inventors: Tasuku Honjo, Kanyu-chi, Oiwake-cho, Kita-Shirakawa, Sakyo-ku, Kyoto, Kyoto; Kei Tashiro, Kyoto; Hideaki Tada, Mishima, all of Japan

[73] Assignees: Tasuku Honjo, Kyoto; Ono Pharmaceutical Co., Ltd., Osaka, both of Japan

[21] Appl. No.: 181,556

[22] Filed: Jan. 14, 1994

[30] Foreign Application Priority Data

Jan. 14, 1993 [JP] Japan .................................... 5-022098

[51] Int. Cl.[6] .................................................. C12N 15/00
[52] U.S. Cl. ............................ 435/69.1; 435/6; 435/69.4; 435/91.2; 435/91.4; 435/91.5; 435/91.51; 435/91.52; 435/183; 435/172.3; 435/320.1; 536/23.1; 536/25.3; 935/78; 935/88
[58] Field of Search ................................ 435/6, 69.1, 69.4, 435/91.2, 91.1, 91.4, 91.5, 91.51, 91.52, 183, 240.1, 172.3, 320.1; 536/22.1, 23.1, 25.3; 935/3, 4, 16, 18, 23, 55, 66, 88

[56] References Cited

U.S. PATENT DOCUMENTS 5,159,062  10/1992  Knapp et al. .......................... 530/350

FOREIGN PATENT DOCUMENTS 0244042  11/1987  European Pat. Off. .
9218521  10/1992  WIPO .

OTHER PUBLICATIONS

Nucl. Acids Res., vol. 19, No. 25, Dec. 1991, IRL Press, Oxford, England, pp. 7097–7104, E. Hara et al, "Subtractive cDNA cloning using oligo(dT)$_{30}$–latex and PCR: isolation of cDNA clones specific to undifferentiated human embryonal carcinoma cells".

Science, vol. 261, 30 Jul. 1993, AAAS, Washington, D.C. (US), pp. 600–603, K. Tashiro et al, "Signal sequence trap: A cloning strategy for secreted proteins and type I membrane proteins".

Proc. Natl. Acad. Sci., vol. 91, No. 6, 15 Mar. 1994, Natl. Acad. Sci., Washington, D.C. (US), pp. 2305–2309, T. Nagasawa et al, "Molecular cloning and structure of a pre–B–cell growth–stimulating factor".

Primary Examiner—W. Gary Jones
Assistant Examiner—Ardin H. Marschel
Attorney, Agent, or Firm—Watson Cole Stevens Davis

[57] ABSTRACT

The present invention relates to (1) a process for constructing a cDNA library which has a selectivity for signal peptides, that makes it possible to efficiently find out an unknown and useful polypeptide and a high efficiency; and relates to (2) a novel polypeptide consisting of 89 amino acids (including a signal peptide) produced by a stroma cell line, which is useful as an agent for preventing or treating, for example, anemia, leukopenia or infections and the like, and DNAs encoding for said polypeptide.

3 Claims, 11 Drawing Sheets

*Figure 4*
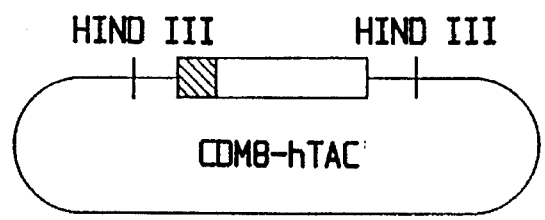
DIGESTING WITH HIND III
SUBCLONING INTO pBS HIND III
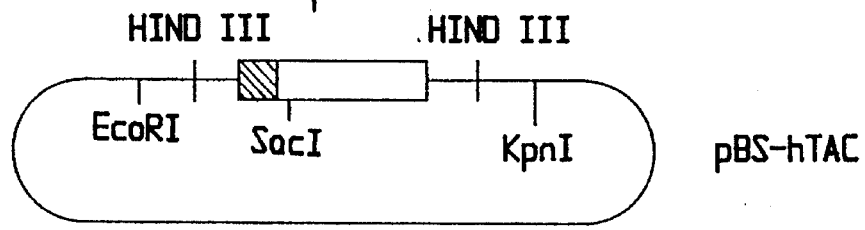
DIGESTING WITH SacI-KpnI
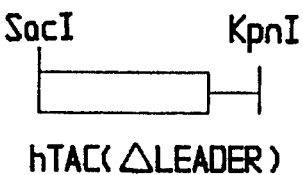

PROCESS FOR CONSTRUCTING CDNA LIBRARY, AND NOVEL POLYPEPTIDE AND DNA CODING FOR THE SAME

FIELD OF THE INVENTION

This invention relates to a process for constructing a cDNA library, and a novel polypeptide and a DNA coding for the same. More particularly, it relates to a process for constructing a cDNA library of a high selectivity for signal peptides and a high efficiency, and a novel polypeptide produced by a specific stroma cell line and a DNA coding for said polypeptide.

RELATED ARTS

In order to obtain a certain polypeptide (for example, a proliferation and/or differentiation factor) or a DNA coding for the same, there has been generally employed a method comprising confirming the target biological activity in a tissue or a cell culture medium and then cloning a gene responsible for the activity through the isolation and purification of a polypeptide and another method comprising expression-cloning of a gene with the guidance of the biological activity.

However, it is frequently observed that a gene, which has been cloned with the guidance of a certain activity, is proved to be identical with a known polypeptide known to have a certain biological activity. This is true because many physiologically active polypeptides occurring in vivo have various biological activities. Further, most of the intravital physiologically active polypeptides are secreted only in a trace amount, which makes the isolation and purification thereof and the confirmation of its biological activity extremely difficult.

Recent rapid developments in techniques for constructing cDNAs and sequencing techniques have made it possible to quickly sequence a large amount of cDNAs. By utilizing these techniques, a process, which comprises constructing cDNA libraries from various cells and tissues, cloning cDNAs at random, identifying the nucleotide sequences thereof, expressing the corresponding polypeptide and then analyzing its physiological functions, is now in progress. Although this process is advantageous in that a gene can be cloned and information regarding its nucleotide sequence can be obtained without effecting any biochemical or genetic analysis, the target gene can be found out thereby only accidentally in many cases.

MEANS FOR SOLVING THE PROBLEMS

The present inventors have studied cloning of genes for proliferation and/or differentiation factors functioning in hematopoietic systems and immune systems. They have focused their attention on the fact that most of the secretory proteins such as proliferation and/or differentiation factors (for example, various cytokines) and membrane proteins such as receptors thereof (hereinafter these proteins will be referred to generally as secretory proteins and the like) have sequences called signal peptides in the N-termini. The inventors in making this initial observation conducted extensive studies on a process for efficiently and selectively cloning a gene coding for a signal peptide. As a result, they have successfully discovered a process whereby an N-terminal fragment can be efficiently amplified and the existence of a signal peptide can be easily examined, thus completing the present invention.

Namely, cDNAs with a high possibility of producing a signal peptide are ligated at their two ends to linkers forming fragments containing restriction enzyme sites which are different from each other. Then these fragments are rapidly produced in a large amount by the polymerase chain reaction (PCR) method. Next, a fragment is introduced into an expression vector having DNA lacking a DNA sequence coding for a signal peptide of a known secretory protein and the like inserted therein, by taking advantage of a characteristic of many secretory proteins and the like of being secreted or expressed on cell membrane even though the signal peptide thereof has been substituted with a signal peptide of another secretory protein and the like. When the known secretory protein and the like is expressed on a cell membrane or outside the cells, therefore, it can be confirmed that the cDNA fragment corresponding to the signal peptide has been properly introduced. Thus the present inventors have established a sure and convenient detection system for establishing the presence of signal peptide.

The polymerase chain reaction has been known as a method for amplifying DNA fragments in a large amount. It is also well known that many secretory proteins and the like can be expressed even though the signal peptide thereof is substituted with that of another secretory protein and the like. However, it has been neither attempted nor expected to combine these findings together; and it has never been known to apply the combination to a process for selectively cloning a signal peptide.

The present invention further relates to a novel polypeptide obtained from hematopoietic cells and a DNA coding for the same. It is known that hematopoietic cells secrete various proliferation and/or differentiation factors exemplified by interleukin. This fact suggests that factors having similar or novel functions might be secreted therefrom in addition to the known secretory factors already found.

The present inventors have paid attention to this point and attempted to find a novel factor (polypeptide) produced by hematopoietic cells with the use of the process which is the first subject of the present invention. As a result, they have successfully found a completely novel polypeptide and a DNA coding for the same, thus completing the present invention.

When polypeptides having sequences identical or highly homologous with that of the polypeptide of the present invention and the DNAs coding for the same are searched for with a computer, none is found. Thus it has been proved that the polypeptide of the present invention and the DNA coding for the same are completely novel ones. Further, the analysis of homology has revealed that the polypeptide of the present invention is a member of chemokine family because it has a pattern of Cys-X-Cys (X is an optional amino acid).

BRIEF DESCRIPTION OF THE DRAWINGS

FIG. 4 is a conceptional view of the process for constructing an SacI-KpnI fragment of hTac cDNA.

DISCLOSURE OF THE INVENTION

Accordingly, the first subject of the present invention is concerned with a process for efficiently constructing a cDNA library of signal peptides.

That is to say, the process for constructing a cDNA library of signal peptides according to the present invention consists of the following steps of:

(1) and (2) synthesizing a single-stranded DNA from mRNA isolated from subject cells with the use of a random primer and adding oligo dT to the 3'-end of the single-stranded DNA thus obtained;

(3) synthesizing a double-stranded DNA from the single-stranded DNA obtained in the above (1) and (2) using as a primer a poly A oligomer ligated to a specific restriction enzyme (enzyme I) site;

(4) and (5) fragmenting the double-stranded DNA obtained in the above (3), fractionating the fragments obtained by size, ligating linker containing a specific restriction enzyme (enzyme II) site, differing from the enzyme I, thereto and fractionating again;

(6) performing a polymerase chain reaction using a first primer containing the enzyme I site and a second primer containing the enzyme II site, digesting the cDNA thus amplified with the enzyme I and enzyme II and fractionating; and (7) and (8) ligating the cDNA fragment upstream of the gene for a known secretory protein or membrane protein with the deletion of its own signal peptide and integrating the ligated DNA into an eucaryotic cell expression plasmid vector, followed by transformation.

Figure 1:
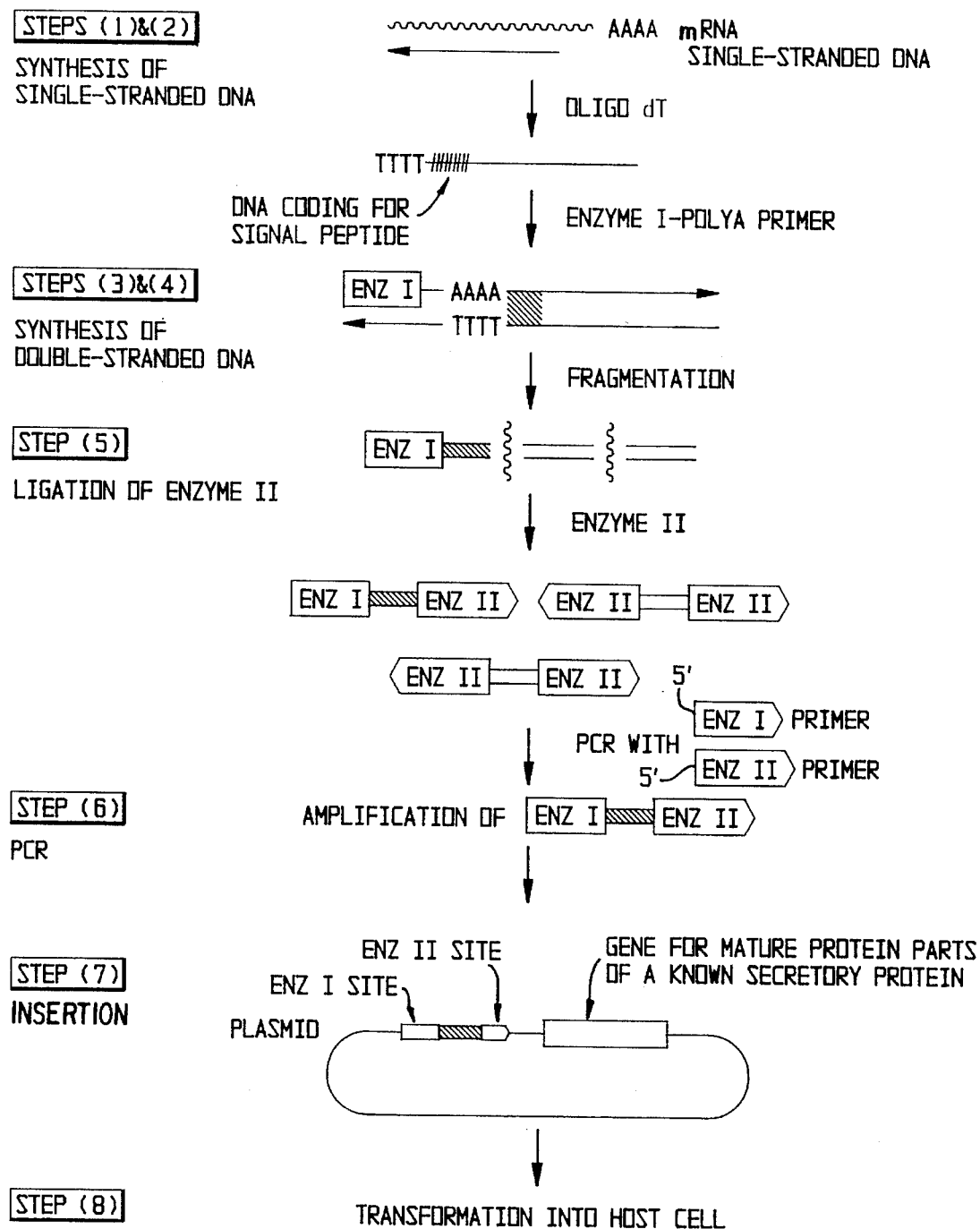
FIG. 1 is a conceptional view of the process for constructing a cDNA library according to the present invention.

FIG. 1 is a conceptional view of the above-mentioned steps.

Now each of these steps will be illustrated in detail. In step (1), the subject cells are stimulated with an appropriate stimulating agent, if required, and then the mRNA is isolated in accordance with known methods as described for example by Okayama H. et al., Methods in Enzymology, 154, 3 (1987).

As the subject cells, any cells may be used, so long as they have a possibility of producing a secretory protein or the like. For example, nerve cells and hematopoietic cells may be cited therefor. Examples of subject cells are Schawnn cells, human glioblastoma cell lines such as T98G, T cells, B cells, human T cell lines such as Jurkat, B21, which is known to secrete Human interleukin. A single-stranded cDNA can be synthesized with the use of a random primer by methods known per se. A marketed random primer is available therefor. Subsequently, in step (2), oligo dT is added to the 3'-end of the single-stranded cDNA by using a terminal deoxytransferase.

In the step (3), a double-stranded cDNA is synthesized by methods known per se. Any restriction enzyme sites may be used as the restriction enzyme (enzyme I) site to be ligated to the poly A oligomer serving as a primer and the restriction enzyme (enzyme II) site to be used in step (5), so long as they differ from each other. Preferably, rare enzyme restriction sites are to be used. More specifically, it is preferable to use EcoRI and SacI, as the enzyme I and the enzyme II, respectively. EcoRI is a comparatively rare enzyme restriction site, and the SACI site accidentally exists in the downstream region of the DNA encoding the signal peptide of interleukin 2 used as a reporter protein. NotI and SaII can also be used.

In the step (4), the double-stranded DNA is fragmented for example by ultrasonication so as to give an average cDNA length of 300 bp and the obtained fragments are fractionated into cDNAs of 200 to 500 bp by agarose gel electrophoresis (AGE). After blunting with T4DNA polymerase, an enzyme II adaptor is ligated in step (5) and the cDNAs are fractionated into DNAs of 200 to 500 bp again by agarose gel electrophoresis. As described above, any enzyme may be used as the enzyme II, so long as it differs from the enzyme I. The procedure in this step elevates a possibility that a cDNA fragment containing a signal peptide exists in the part located between the enzyme restriction sites I and II.

In step (6), PCR is carried out in order to elevate the number of cDNA fragments containing a signal peptide. PCR is a well known technique and automated devices therefore are commercially available. It is sufficient to amplify 25 to 30 times. The cDNA thus amplified is digested with the enzyme I–enzyme II and electrophoresed on an agarose gel to thereby fractionate into cDNAs of 200 to 500 bp.

In the step (7), a gene for a known secretory protein and the like with the deletion of signal peptide, which is called a reporter gene, and a cDNA fragment obtained in the above step (6) are integrated into an eucaryotic cell expression plasmid vector in such a manner that the cDNA fragment is located upstream of the reporter gene. This is followed by transformation of the vector into a host in step (8). From among various eucaryotic cell expression plasmid vectors which have already been known, for example, pcDL-SRα and pcEV-4 capable of acting in *Escherichia coli* are available in the present invention.

As the reporter gene, genes for mature protein parts of soluble secretory proteins and membrane proteins of any type are usable. The expression of these reporter genes may be confirmed by some methods such as an antibody method. It is suitable to use human IL-2 receptor α gene therefor. There have been known a number of *E. coli* strains available as hosts for in transformation and any of these stains is usable. It is preferable to use DH5 competent cells [described in Gene, 96, 23 (1990)] therefor. Transformants may be incubated in a conventional manner and thus the cDNA library of the present invention can be obtained.

In the process for constructing a cDNA library according to the present invention, there is a high possibility that gene fragments coding for signal peptides are contained in the library. However, not every clone contains said fragment. Further, not all of the gene fragments code for unknown (novel) signal peptides. It is therefore necessary to screen a gene fragment coding for an unknown signal peptide from said library.

Namely, the cDNA library is divided into small pools of an appropriate size and integrated into an expression system.

Examples of the expression system for producing a polypeptide include mammalian cells (for example, monkey COS-7 cells, Chinese hamster CHO cells, mouse L cells, etc.). Transfection may be performed in accordance with well known methods such as the DEAE-dextran method. After the completion of the incubation, the expression of the reporter gene is examined. It is known that a reporter gene would be expressed even though the signal peptide is characteristic of another secretory protein. That is to say, the fact that the reporter gene has been expressed indicates that a signal peptide of some secretory protein has been integrated into the library. Positive pools are further divided into smaller ones and the expression and the judgement are repeated until a single clone is obtained. The expression of the reporter gene can be judged by, for example, fluorescence-labeled antibody assay, enzyme-linked immunosorbent assay (ELISA) or radioimmunoassay (RIA), depending on kinds of the employed reporter gene.

Next, the nucleotide sequence of the isolated positive clone is determined. In the case of a cDNA which is proved to code for an unknown protein, the clone of the full length is isolated with the use of the cDNA as a probe and the full nucleotide sequence can be thus identified. All of these operations are carried out by methods which are well known by those skilled in the art. For example, the nucleotide sequence may be identified by the Maxam-Gilbert method or the dideoxy terminator method. On the other hand, the full length is sequenced in accordance with a method described in Molecular Cloning [Sambrook, J., Fritsch, E. F. and Manfalls, T., published by Cold Spring Harbor Laboratory Press in 1989].

The second subject of the present invention is concerned with a polypeptide having the amino acid shown in SEQ ID. No. 2 in substantially purified form, a homologue thereof or a fragment of the sequence or homologue of a fragment, and DNA encoding such a polypeptide. The polypeptide having the sequence shown in SEQ ID No. 2 has been identified using the process of the invention. In particular, it relates to:

(1) a polypeptide consisting of an amino acid sequence represented by SEQ ID No. 2;

(2) a DNA coding for the polypeptide described in the above(1);

(3) a DNA having a nucleotide sequence represented by SEQ ID No. 1 at location 82 to 348; and (4) a DNA having a nucleotide sequence represented by SEQ ID No. 3.

A polypeptide of Seq. ID No. 2 in substantially purified form will generally comprise the polypeptide in a preparation in which more than 90%, e.g., 95%, 98% or 99% of the polypeptide in the preparation is that of the Seq. ID No. 2.

A polypeptide homologue of the Seq. ID No. 2 will be generally at least 70%, preferably at least 80 or 90% and more preferably at least 95% homologous to the polypeptide of Seq. ID No. 2 over a region of at least 20, preferably at least 30, for instance 40, 60, 70 or more contiguous amino acids. Such polypeptide homologues will be referred to below as a polypeptide according to the invention.

Generally, fragments of Seq. ID No. 2 or its homologues will be at least 10, preferably at least 15, for example 20, 25, 30, 40, 50 or 60 amino acids in length, and are also encompassed by the term "a polypeptide according to the invention" as used herein. Particular fragments of the polypeptides of the invention are fragments of which include amino acid residues numbered 1–70 in Seq. ID No. 2 or a homologue thereof.

A DNA capable of selectively hybridizing to the DNA of Seq. ID No. 1 or 3 will be generally at least 70%, preferably at least 80 or 90% and more preferably at least 95% homologous to the DNA of Seq. ID No. 1 or 3 over a region of at least 20, preferably at least 30, for instance 40, 50 or 100 or more contiguous nucleotides. Such DNA will be encompassed by the term "DNA according to the invention". Particular DNA capable of selectively hybridizing to the DNA of Seq. ID No. 1 or 3, of the invention are nucleotide residues numbered 139–348 in Seq. ID No. 1 or fragments thereof.

DNA according to the invention may be used to produce a primer, e.g., a PCR primer, a probe, e.g., labelled by conventional means using radioactive or non-radioactive labels, or the DNA may be cloned into a vector. Such primers, probes and other fragments of the DNA of Seq. ID No. I or 3 will be at least 15, preferably at least 20, for example 25, 30 or 40 nucleotides in length, and are also encompassed by the term "DNA according to the invention" as used herein.

DNA according to the invention may be produced recombinantly, synthetically, or by any means available to those of skill in the art.

A further embodiment of the invention provides replication and expression vectors comprising DNA according to the invention. The vectors may be, for example, plasmid, virus or phage vectors provided with an origin of replication, optionally a promoter for the expression of the said DNA and optionally a regulator of the promotor. The vector may contain one or more selectable marker genes, for example an ampicillin resistance gene. The vector may be used in vitro, for example for the production of RNA corresponding to the DNA, or used to transform a host cell.

A further embodiment of the invention provides host cells transformed or transfected with the vectors for the replication and expression of DNA according to the invention, including the DNA Seq. ID No. 1 or 3 or the open reading frame thereof. The cells will be chosen to be compatible with the vector and may for example be bacterial, yeast, insect or mammalian.

DNA according to the invention may also be inserted into the vectors described above in an antisense orientation in order to provide for the production of antisense RNA (DNA). Antisense RNA (DNA) may also be produced by synthetic means. Such antisense RNA (DNA) may be used try a method of controlling the levels of a polypeptide of the invention in a cell.

A further embodiment of the invention provides a method of producing a polypeptide which comprises culturing host cells of the present invention under conditions effective to express a polypeptide of the invention. Preferably, in addition, such a method is carried out under conditions in which the polypeptide of the invention is expressed and then secreted from the host cells.

The invention also provides monoclonal or polyclonal antibodies to a polypeptide according to the invention. The invention further provides a process for the production of monoclonal or polyclonal antibodies to the polypeptides of the invention. Monoclonal antibodies may be prepared by conventional hybridoma technology using a polypeptide of the invention or a fragment thereof, as an immunogen. Polyclonal antibodies may also be prepared by conventional means which comprise inoculating a host animal, for example a rat or a rabbit, with a polypeptide of the invention and recovering immune serum.

The present invention also provides pharmaceutical compositions containing a polypeptide of the invention, or an antibody thereof, in association with a pharmaceutically acceptable diluent or carrier.

The invention also provides a polypeptide according to the invention or an antibody for use in a method of therapy or diagnosis on a human or animal body.

The polypeptide of the present invention involves not only those having the amino acid sequence represented by the sequence No. 1 but also those with partial deletion thereof (for example, a polypeptide consisting of the mature protein part alone, or consisting of a part of the mature protein essentially required for the expression of the biological activity), those with partial replacement by other amino acid(s) (for example, a polypeptide some of amino acids of which are replaced by those having similar properties) and those with partial addition or insertion of amino acid(s).

It is well known that there are up to six different codons which may code for a single amino acid (for example, one type of codon for Met while six types of codon for Leu). Accordingly, the nucleotide sequence of the DNA can be changed without altering the amino acid sequence of the polypeptide.

The DNA as specified in (2) involves all nucleotide sequences coding for the polypeptide of (1) represented by Seq. ID No. 2. Changes in the nucleotide sequence sometimes bring about an increase in the polypeptide productivity.

The DNA as specified in (3) is an embodiment of the DNA as specified in (2) and represents a natural sequence.

The DNA as specified in (4) also shows a sequence wherein a natural non-translational region is added to the DNA as specified in (3).

A signal peptide is a highly hydrophobic region located immediately downstream of the translation initiation amino acid Met. It is assumed that the signal peptide in the polypeptide of the present invention resides in a region ranging from Met at the 1-position to Ser at the 19-position in the amino acid sequence represented by Seq. ID No. 2. The region essentially responsible for the expression of the biological activity corresponds to the part of the amino acid sequence of the Seq. ID No. 2 lacking of the signal peptide, i.e., the mature protein part. Thus the signal peptide number relates to the activity.

The DNA having the nucleotide sequence represented by Seq. ID No. 1 can be prepared in accordance with the process described as the first subject of the present invention.

Once the nucleotide sequences represented by Seq. ID No. I and No. 3 are determined, the DNA of the present invention can be chemically synthesized. Alternatively, the DNA of the present invention can be obtained by chemically synthesizing fragments of said nucleotide sequence and hybridizing with the use of the fragments as a probe. Further, the target DNA can be produced in a desired amount by introducing a vector DNA containing said DNA into an appropriate host and then incubating the host.

Examples of methods for obtaining the polypeptide of the present invention include:

(1) isolation and purification from vital tissues or cultured cells;

(2) chemical synthesis of peptides; and (3) production with the use of gene recombination techniques. From an industrial viewpoint, the method described in (3) is preferable.

Examples of the expression system (host-vector system) for producing the polypeptide by using gene recombination techniques include those of bacteria, yeasts, insect cells and mammalian cells.

In order to express in E. coli, for example, an initiator codon (ATG) is added to the 5'-end of the DNA coding for the mature protein region. The DNA thus obtained is then ligated to the downstream of an appropriate promoter (for example, trp promoter, lac promoter, λpL promoter, T7 promoter, etc.) and inserted into a vector capable of functioning in E. coli (for example, pBR322, pUC18, pUC19, etc.), thus constructing an expression vector. Next, an E. coli strain (for example, E. coil DH1, E. coli JM109, E. coli HB101, etc.) transformed with this expression vector is incubated in an appropriate medium. Thus the target polypeptide can be obtained from the incubated cells. Alternately, a bacterial signal peptide (for example, a signal peptide of peIB) may be used and thus the polypeptide can be secreted into the periplasm. Furthermore, a fusion protein together with other polypeptide can be produced.

Expression in mammalian cells can be effected, for example, in the following manner. Namely, a DNA coding for the nucleotide sequence represented by Seq. ID No., 3 is inserted into the downstream end of an appropriate promoter (for example, SV40 promoter, LTR promoter, metallothionein promoter, etc. ) in an appropriate vector (for example, retrovirus vector, papilloma virus vector, vaccinia virus vector, SV40-series vector, etc.), thus constructing an expression vector. Next, appropriate mammalian cells (for example, monkey COS-7 cells, Chinese hamster CHO cells, mouse L cells, etc.) are transformed with the expression vector obtained above and the transformant is incubated in an appropriate medium. Thus the target polypeptide can be secreted into the culture medium. The polypeptide thus obtained can be isolated and purified by conventional biochemical methods.

EFFECTS OF THE INVENTION

By using the process for constructing a cDNA library which is the first subject of the present invention, a DNA coding for a signal peptide of a secretory protein or a membrane protein can be efficiently selected and, in its turn, an unknown and useful protein can be efficiently found. The novel polypeptide which is the second subject of the present invention is produced and secreted from a stroma cell line. Therefore, the polypeptide has biological activities relating to the survival and proliferation of hematopoietic stem cells and the proliferation and differentiation of B cells and myeloid cells, and chemoattractant activity or neurophil. Accordingly, the polypeptide of the present invention per se is usable as an agent for preventing or treating, for example, anemia or leukopenia, infections, etc.

APPLICATION FOR PHARMACEUTICALS

For the purpose of the prevention of or in the treatment of anemia or leukopenia, infections, etc., the polypeptide of the present invention may be administered systemically or partially, usually by oral or parenteral administration, preferably orally or intravenously.

The doses to be administered are determined depending upon age, body, weight, symptom, the desired therapeutic effect, the route of administration, and the duration of treatment, etc., In the human adult, the doses per person per dose are generally between 100 μg and 100 mg, by oral administration, up to several times per day, and between 10 μg and 100 mg, by parenteral administration up to several times per day.

As mentioned above, the doses to be used depend upon various conditions. Therefore, there are cases in which doses lower than or greater than the ranges specified above may be used.

Administration of the compounds of the present invention, may be as solid compositions, liquid compositions or other compositions for oral administration, as injections, liniments or suppositories, etc., for parenteral administration.

Solid compositions for oral administration include compressed tablets, pills, capsules, dispersible powders, and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate etc.) The compositions may also comprise, as is normal practice, additional substances other than inert diluents: e.g., lubricating agents (such as magnesium stearate etc.), disintegrating agents (such as cellulose calcium glycolate etc.), stabilizing agents (such as human serum albumin, lactose, etc.), and assisting agents for dissolving (such as arginine, asparaginic acid, etc.)

The tablets or pills may, if desired, be coated with film of gastric or enteric material (such as sugar, gelatin, hydroxypropyl cellulose or hydroxypropylmethyl cellulose phthalate etc.), or be coated with more than two films. And further, the coating may include containment within capsules or absorbable materials such as gelatin.

Liquid compositions for oral administration include pharmaceutically-acceptable solutions, emulsions, suspensions, syrups and elixirs.

In such compositions, one or more of the active compound(s) is or are in inert diluent(s) commonly used in the art (purified water, ethanol, etc.).

Besides inert diluents, such compositions may also comprise adjuvants (such as wetting agents, suspending agents, etc.), sweetening agent, flavoring agents, perfuming agents and preserving agents.

Other compositions for oral administration include spray compositions which may be prepared by known methods and which comprise one or more of the active compound(s).

Spray compositions may comprise additional substances other than inert diluents: e.g., stabilizing agent s(sodium sulfite, etc.), isotonic buffer (sodium chloride, sodium citrate, citric acid, etc.)

For preparation of such spray compositions, for example, the method described in U.S. Pat. No. 2,868,691 or U.S. Pat. No. 3,095,355 (herein incorporated in their entireties by reference) may be used.

Injections for parenteral administration include sterile aqueous or non-aqueous solutions, suspensions and emulsions. In such compositions, one or more active compound(s) is or are administered with at least one inert aqueous diluent(s) (distilled water for injection, physiological salt solution, etc.) or inert non-aqueous diluent(s) (Propylene glycol, polyethylene glycol, olive oil, ethanol, POLYSOLBATE 80®, etc.)

Injections may comprise additions other than inert diluents: e.g., preserving agents, wetting agents, emulsifying agents, dispersing agents, stabilizing agent (such as human serum albumin, lactose, etc.)., and assisting agents such as assisting agents for dissolving (such as arginine, asparaginic acid, etc.)

They may be sterilized, for example by filtration through a bacteria-retaining filter, by incorporation of sterilizing agents in the compositions or by irradiation. They also can be manufactured in the form of sterile solid compositions, for example, by freeze-drying, and which can be dissolved in sterile water or some other sterile diluents for injection immediately before use.

Other compositions for parenteral administration include liquid for external use, and endermic liniments (ointment, etc.)., suppositories and pessaries which comprise one or more of the active compound(s) and may be prepared by known methods.

In addition, the above-mentioned polypeptide existing in vivo can be assayed by using a polyclonal antibody or a monoclonal antibody for said polypeptide, which is applicable to studies on the relationship between said polypeptide and diseases or to the diagnosis of diseases and the like. The polyclonal antibody and the monoclonal antibody can be prepared by a conventional method with the use of said polypeptide or a fragment thereof as an antigen.

The DNA according to the present invention serves as an important and essential template in the production of the polypeptide of the present invention which is expected to be highly useful. Further, the DNA of the present invention is applicable to the diagnosis and treatment of hereditary diseases, i.e., gene therapy, and therapy with ceasing the expression of the polypeptide by using antisense DNA (RNA). Furthermore, a genomic DNA can be isolated by using the DNA of the present invention as a probe. Similarly, a human gene for a related polypeptide being highly homologous with the DNA of the present invention and a gene of an organism other than human for a polypeptide being high homologous with the polypeptide of the present invention can be isolated.

EXAMPLES

The following Examples and Reference Example are illustrated, but not limit the present invention.

REFERENCE EXAMPLE 1

Construction and expression of plasmid pcDL-SRα-h-G-CSF-hTac (pSGT) and plasmid pcDL-SRα-hRARα-hTac (pSRT)

A plasmid, wherein a cDNA coding for a fusion protein of hG-CSF (human granulocyte colony stimulating factor, a typical example of a protein having a signal peptide) or hRARα (human retinoic acid receptor α, a typical example of a protein having no signal peptide), with hTac (human IL-2 receptor α, used as a reporter gene) was integrated into an eucaryotic cell expression plasmid vector pcDL-SRα having an SRα promoter [described in Mol. Cell. Biol., 8, 466(1988), provided by Dr. Yutaka Takebe, National Institute of Health], was constructed. After transformation, the expression of the reporter protein on the membrane was examined.

(1) By employing a plasmid pSP72-hG-CSF, wherein hG-CSF cDNA had been integrated into the EcoRI site of a plasmid pSP72 (purchased from Promega), as a template and using an SP6 promoler primer (purchased from Takara Shuzo Co., Ltd.) and an hG-CSF specific primer having an SacI site added thereto, 5' GGA<u>GATATC</u>GAGCT<u>CC</u>TCGGGGTGGCACAG 3'  (SEQ ID NO. 9)
    EcoRV  SacI

|_____|
    hG-CSF cDNA antisense

Figure 2:
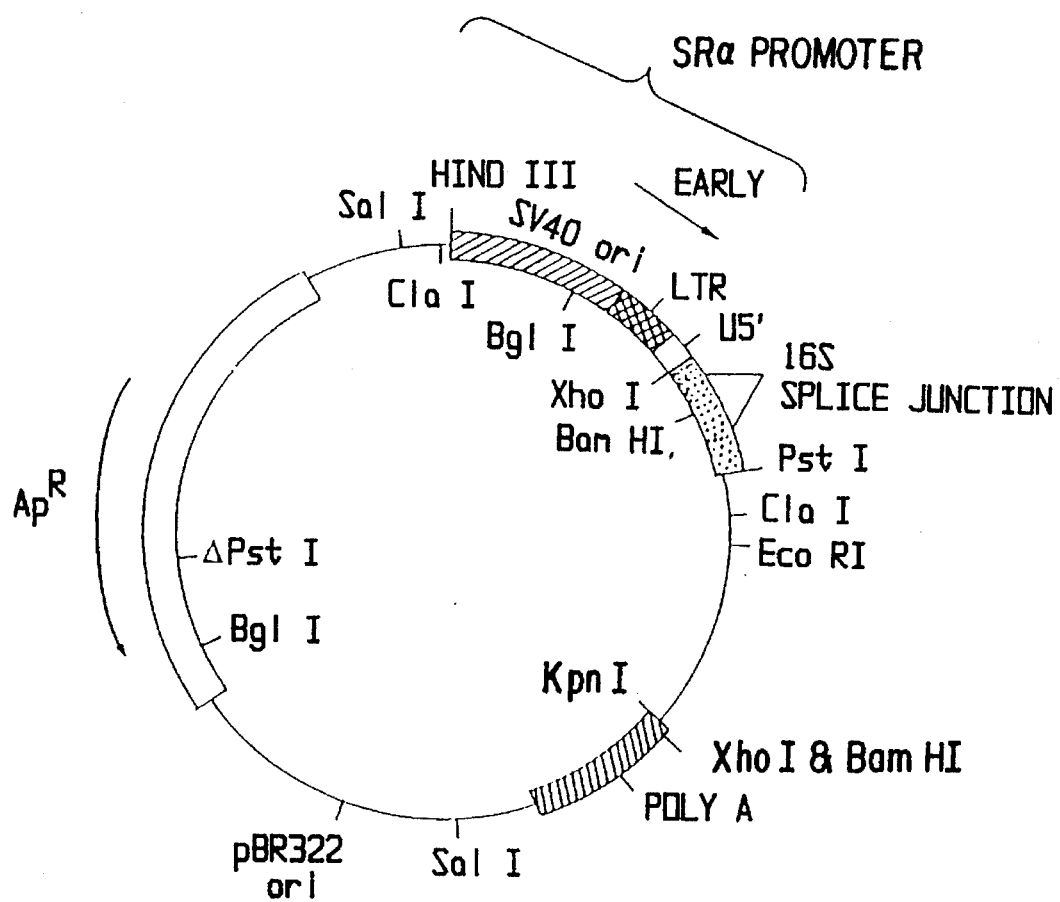
FIG. 2 is a flow chart for the construction of a plasmid vector pcDL-SRα.
Figure 3:
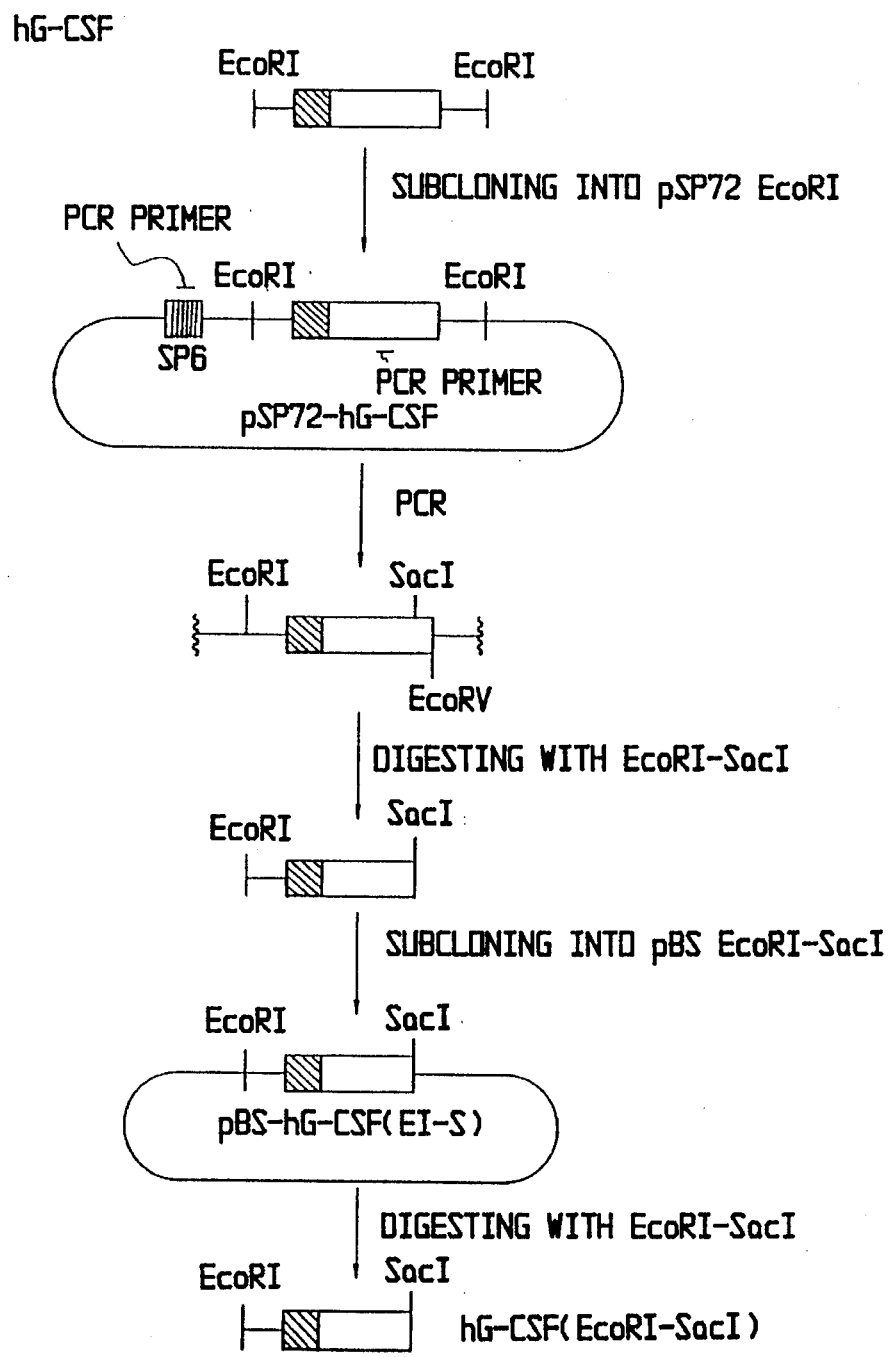
FIG. 3 is a conceptional view of the process for constructing an EcoRI-SacI fragment of hG-CSF.
Figure 5:
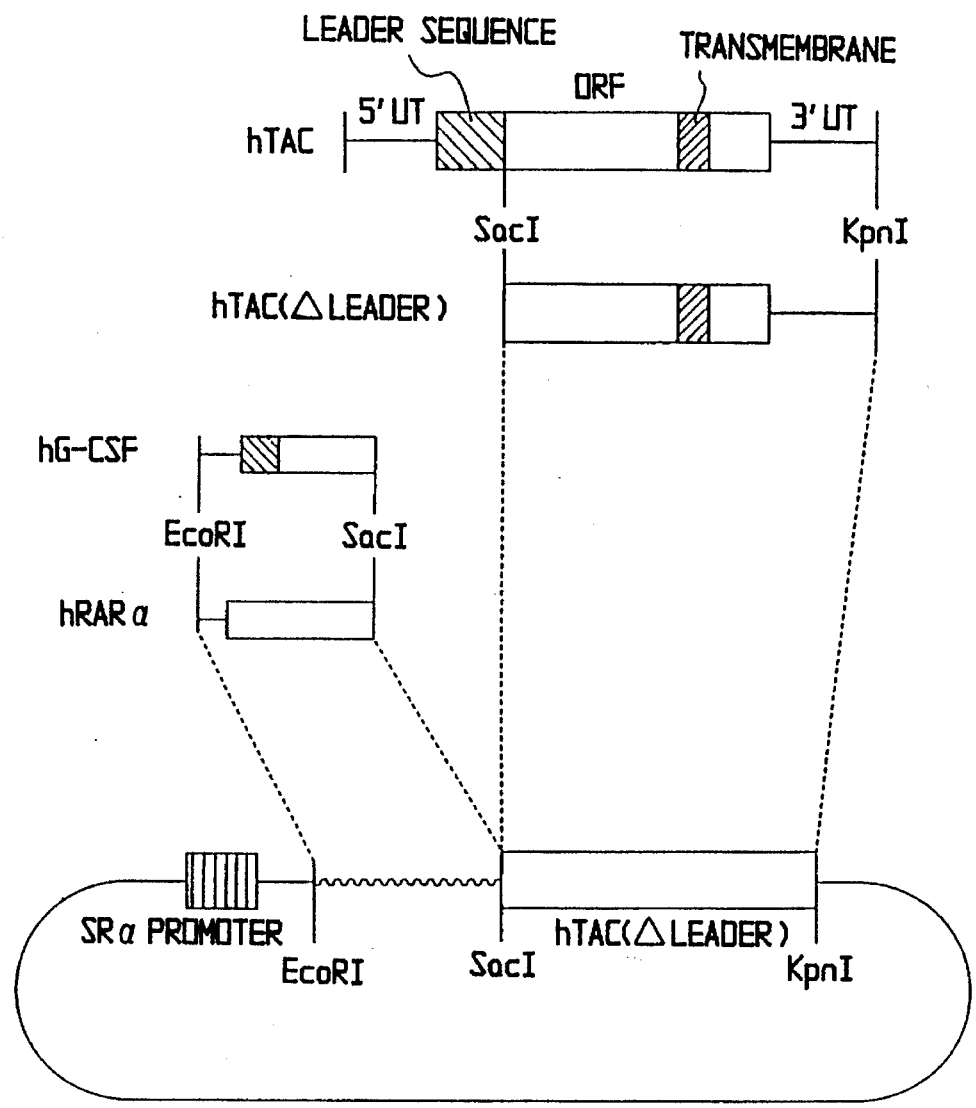
FIG. 5 is a flow chart for the construction of pSGT and pSRT.

PCR was performed 25 cycles (at 95° C. for one minute, at 48° C. for two minutes and at 72° C. for two minutes). The amplified DNA fragment was digested with SacI-EcoRI and once subcloned into a plasmid pBlue script SK(+)(pBS). After digesting with SacI-EcoRI again, an EcoRI-SacI fragment of hG-CSF was obtained. On the other hand, a plasmid pBS-hTac, wherein hTac cDNA had been integrated into the HindIII site of pBS, was digested with SacI-KpnI to thereby give an SacI-KpnI fragment of hTac cDNA with the deletion of the signal sequence. These fragments were integrated into the EcoRI-KpnI site of pcDL-SRα with the deletion of stuffer (FIG. 2) to thereby give a plasmid pcDL-SRα-hG-CSF-hTac (pSGT) (FIGS. 3, 4 and 5).

Next, by employing a plasmid pGEM3-hRARα, wherein hRARα cDNA had been integrated into the EcoRI site of a plasmid pGEM3, as a template and using an SP6 promoter primer and an hRARα specific primer having an SacI site added thereto, 5' GGA<u>GATATC</u> <u>GAGCTC</u>AATGGTGGCTGGGGATG 3' (SEQ ID NO. 4)
    EcoRV  SacI

|_____|
    hRARα cDNA antisense

Figure 6:
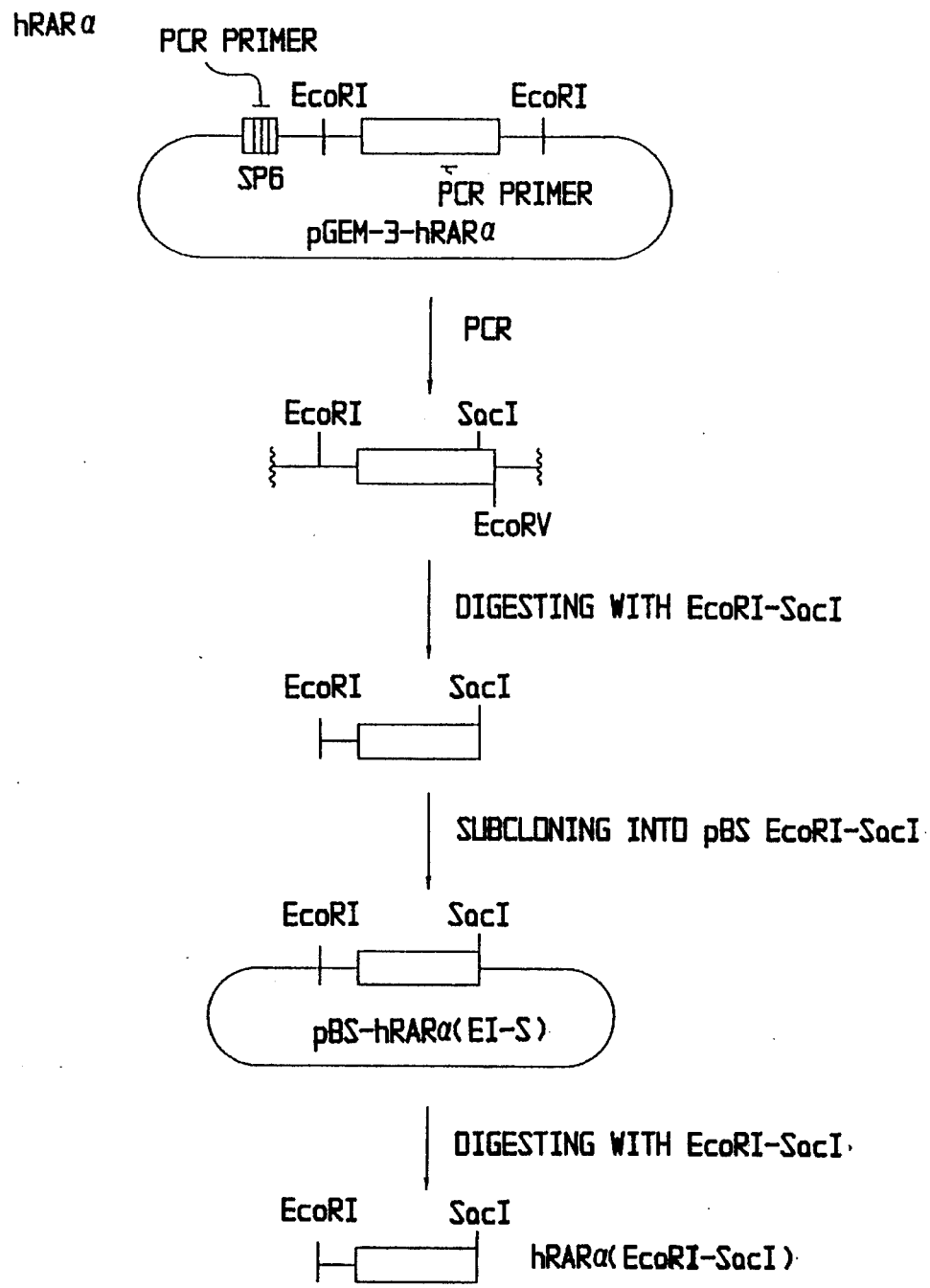
FIG. 6 is a conceptional view of the process for constructing an EcoRI-SacI fragment of hRARα.

PCR was performed. Subsequently, the procedure employed in the above-mentioned case of G-CSF was repeated to thereby give a plasmid pcDL-SRα-hRARα-hTac (pSRT) (FIGS. 6, 4 and 5).

Figure 7:
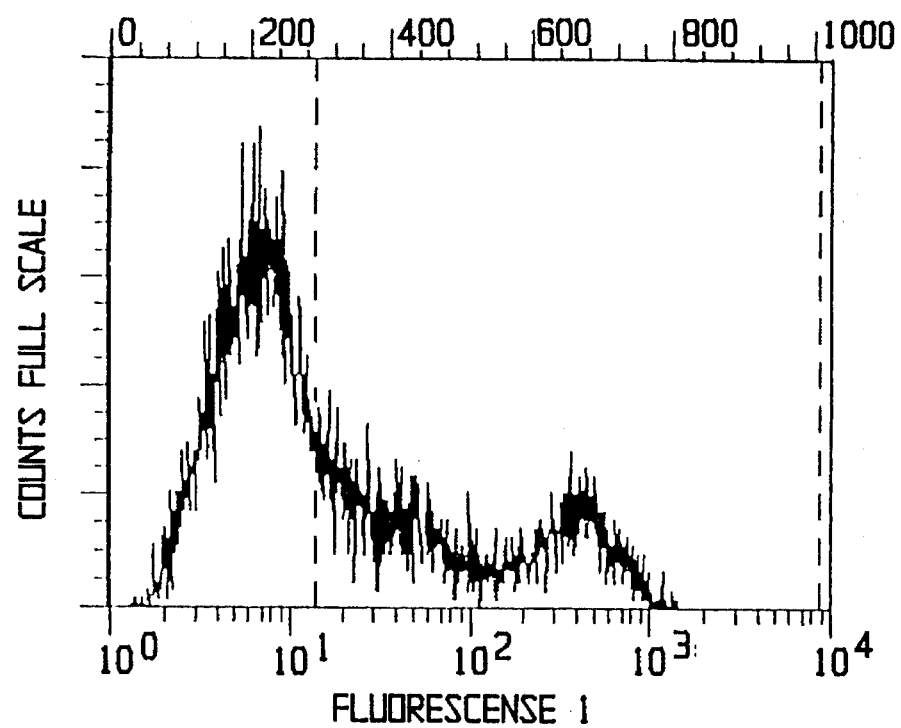
FIG. 7 is an FACS histogram showing the expression of a fusion protein hG-CSF-hTac on membrane.
Figure 8:
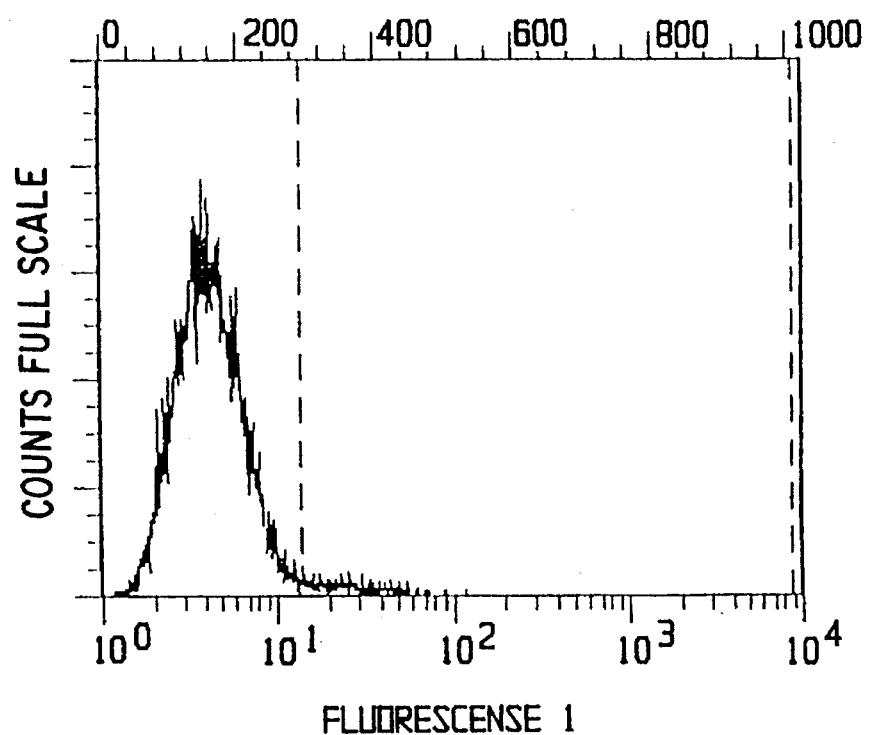
FIG. 8 is an FACS histogram showing the expression of a fusion protein hRAR-hTac on membrane.

(2) The pSGT or pSRT obtained in the above (1) was transfected into COS-7 cells by the DEAE-dextran method [described in detail in Current Protocol in Molecular Biology, chapter 9.2.1.]. After 48 hours, the cells were harvested from a dish and incubated together with mouse anti-Tac IgG antibody for 20 minutes on ice. After eliminating free antibodies, the mixture was incubated together with goat anti-mouse IgG antibody labeled with fluorescein isothiocyanate (FITC) for 20 minutes on ice. After eliminating free antibodies again, the expression of a fusion protein G-CSF-Tac or RARα-Tac on the membrane was examined with a fluorescence activated cell sorter (Model FACS Can, manufactured by BECTON DICKINSON, hereinafter referred to simply as FACS). FIGS. 7 and 8 show the results of the judgement.

As shown in FIG. 7, G-CSF-Tac was expressed on the membrane as well as Tac. As shown in FIG. 8, on the other hand, RARα-Tac was not detected on the membrane but remained within the cells. These results indicate that when a cDNA fragment containing a signal peptide is ligated to the upstream of a reporter gene, said reporter protein is expressed on the cell membrane, while when a cDNA fragment having no signal peptide is ligated, the reporter protein is not expressed.

EXAMPLE 1

Figure 9:
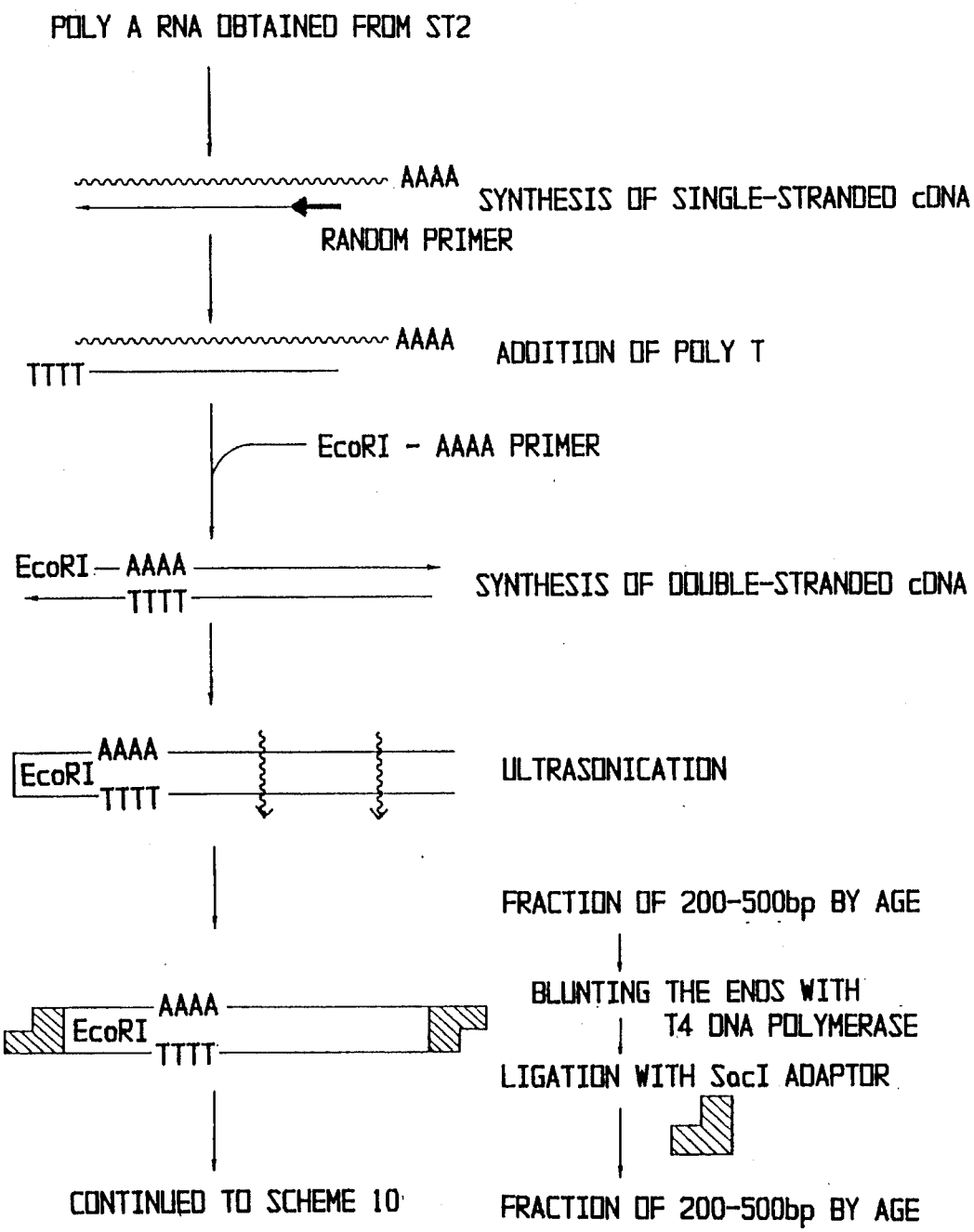
FIG. 9 is a conceptional view (the former half) of the process for constructing the cDNA library of the Example.
Figure 10:
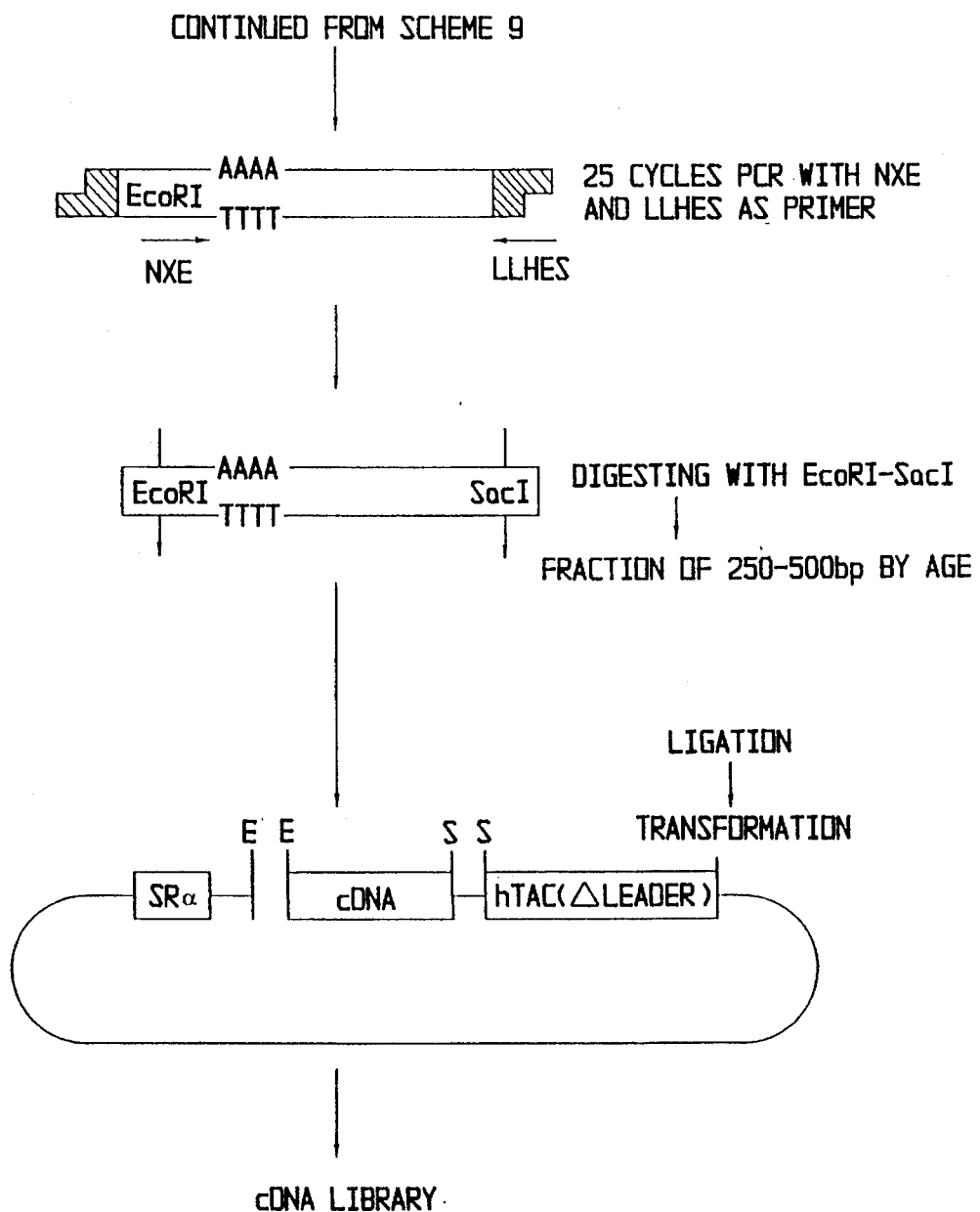
FIG. 10 is a conceptional view (the latter half) of the process for constructing the cDNA library of the Example.

Construction of cDNA library having selectivity for signal peptides (FIGS. 9 and 10)

Total RNA was extracted from a mouse stroma cell line ST2 [cells supporting the survival and proliferation of hematopoietic stem cells and the proliferation and differentiation of B cells and myeloid cells; refer to EMBO J., 7, 1337 (1988)] by the acid guanidine-phenol-chloroform (AGPC) method [described in detail in "Saibo Kogaku Jikken Protokoru (Protocol in Cellular Engineering Experiments)", published by Shujun-sha, 28–31]. Then poly ARNA was purified by using oligo (dT)-latex (Oligotex-dT30®, marketed from Takara Shuzo Co., Ltd.). By using a random hexamer as a primer, a single-stranded cDNA was synthesized with reverse transcriptase and dT was added to the 3'-end thereof with the use of terminal deoxytransferase. A 17 mer dA ligated to a restriction enzyme site containing EcoRI 5' GAT<u>GCGGCCGC</u> <u>CTCGAG</u> <u>GAATTC</u> (dA)₁₇ 3'  (SEQ ID NO. 11)
    NotI      XhoI    EcoRI was annealed and a double-stranded cDNA was synthesized by using the same as a primer. Then the cDNA was fragmented by ultrasonication so as to give an average length of 300 bp and the cDNAs of 200 to 500 bp were fractionated by agarose gel electrophoresis. After blunting the ends with T4DNA polymerase, a lone linker containing an SacI site

5' GAGGTACAAGCTT GATATC GAGCTCGCGG 3'  (SEQ ID NO. 6)

3'      CATG<u>TTCGAA</u> <u>CTATAG</u> <u>CTCGAG</u>CGCC 5'  (SEQ ID NO. 10)
     HindIII   EcoRV   SacI

[see Nucleic Acids Res., 18, 4293 (1990)] was ligated and cDNAs of 200 to 500 bp were fractionated again by agarose gel electrophoresis. By using a primer (NLC) containing an EcoRi site.

NLC                                                          (SEQ ID NO. 5)
5' GATGCGGCCGCCTCGAGGAATTC 3' and another primer (LLHES) containing an SacI site

LLHES                                              (SEQ ID NO. 6)
5' GAGGTACAAGCTTGATATCGAGCTCGCGG 3'

PCR was performed 25 cycles (at 94° C. for one minute, at 50° C. for two minutes and at 72° C. for two minutes). The amplified cDNA was digested with SacI and EcoRI and cDNAs of 250 to 500 bp were fractionated by agarose gel electrophoresis. The cDNA was ligated to a plasmid obtained by digesting pSRT (prepared in Reference Example 1) with SacI and EcoRI by using T4 DNA ligase. After transformation of an E. coli DH5α strain, a cDNA library having a selectivity for signal peptides was obtained.

EXAMPLE 2

Screening and analysis of cDNA coding for signal peptide

About 1,200 colonies in the library obtained in Example 1 were divided into 24 pools (about 50 colonies/pool). Plasmids of each pools were isolated by the miniprep method and transfected into COS-7 cells by the DEAE-dextran method. After 48 to 72 hours, cell surface-staining for Tac of the transfectant was performed in the same manner as described in Reference Example 1 and 6 positive pools were selected under a fluorescent microscope. Colonies of one pool from among the 6 positive pools were further divided and the same procedure as described above was repeated until a single clone was obtained. Thus a positive clone (pS-TT3) was obtained. Subsequently, by using two synthetic primers 5' TTTACTTCTAGGCCTGTACG 3'            (SEQ ID NO. 7)
(20 bases upstream from EcoRI cloning site, for sense)

and

Figure 11:
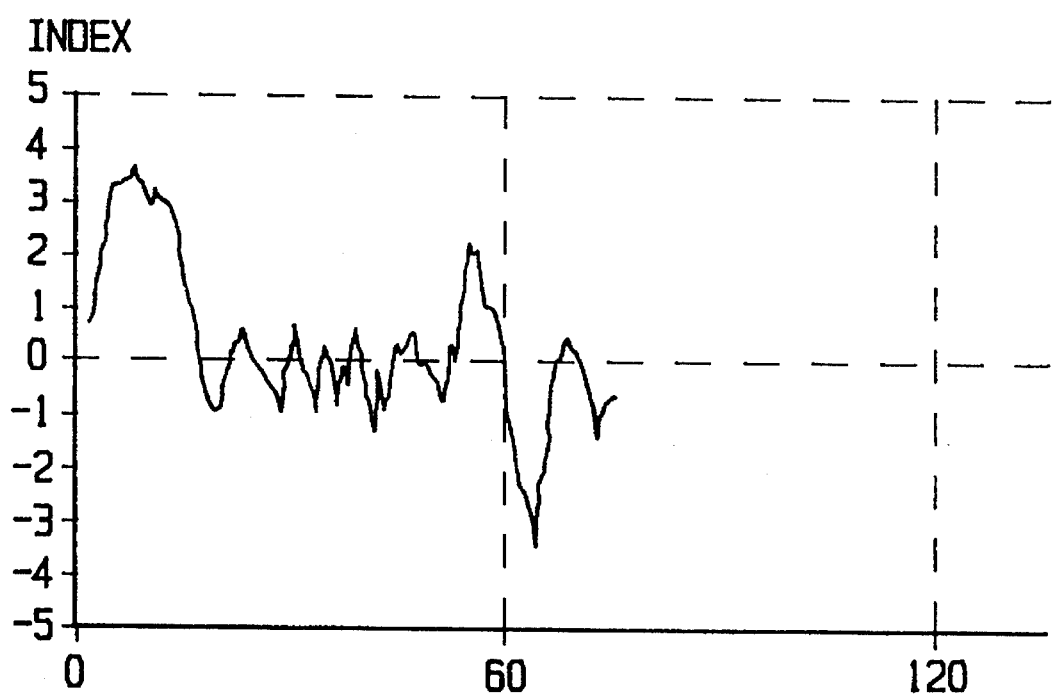
FIG. 11 is a hydrophobicity profile of (a part of) the polypeptide according to the present invention.

5' CCATGGCTTTGAATGTGGCG 3'            (SEQ ID NO. 8)
(20 bases downstream from SacI cloning site, for antisense)

which were specific for the pcDL-SRα-Tac vector, the nucleotide sequence of the TT3 insert was determined. An open reading frame following the Tac cDNA with the deletion of the signal sequence in-frame was searched and converted into the deduced amino acid sequence. After performing a hydrophobicity profile, it was confirmed that a hydrophobic region characteristic to a signal peptide was contained therein (FIG. 11). Further, the homology with data base on DNA and amino acid levels was examined. As a result, it has been found out that TT3 clone codes for an unknown protein.

EXAMPLE 3

Screening of cDNA with the full length and determination of nucleotide sequence

A cDNA library was constructed by using Super Script® Ramda System (marketed from BRL). Next, pS-TT3 was digested with SacI and EcoRI and a TT3 cDNA fragment was prepared by agarose gel electrophoresis. The library was screened by using an oligo-labeled TT3 cDNA fragment as a probe and thus a number of positive clones were obtained. Among these clones, a TT3 -1-6 clone showing the longest insert was selected and an SaII-NotI fragment excised from a λgt22A vector was subcloned into pBS to thereby give a plasmid pBS-TT316. By using a T7 primer, the nucleotide sequence of 300 bp in the 5'-terminal of TT3-1-6 cDNA was determined. Thus it was confirmed that the sequence identical with TT3 of the probe existed in the most 5'-end of TT3-1-6.

Next, a number of pBS-TT316 variant plasmids lacking of the 5'-end or the 3'-end of TT3-1-6 cDNA were constructed by using an ExoIII/Mung Bean Deletion Kit (manufactured by Stratagene). By using these variant plasmids, the nucleotide sequence of the full length of the cDNA was determined (sequence No. 3). From the full length cDNA sequence data, an open reading frame was determined and further translated into an amino acid sequence. Thus the sequence represented by the sequence No. 2 was obtained. The amino acid sequence at the 30- to 40-positions in the N-terminal of the amino acid sequence thus obtained were compared with known signal peptides. Thus the signal peptide part of this polypeptide was deduced to thereby give the sequence represented by the sequence No. 2 at location 82 to 138.

---

What we claim is:

1. A process for constructing a cDNA library enriched for cDNAs coding for signal peptides, comprising the following steps:

(1) synthesizing a single-stranded cDNA from mRNA isolated from subject cells with the use of a random primer;

(2) adding oligo dT to the 3'-end of the single-stranded cDNA obtained in step 1;

(3) synthesizing a double-stranded cDNA from the single-stranded cDNA obtained in step (2) using as a primer a poly A oligomer ligated to a specific restriction enzyme (enzyme I) site to generate double-stranded cDNA containing the enzyme I site on only one end;

(4) fragmenting the double-stranded cDNA generated in step (3) to generate cDNA fragments, wherein at least one fragment contains the enzyme I site on only one end;

(5) ligating a linker containing a specific restriction enzyme (enzyme II) site to the cDNA fragments obtained in step (4) to generate at least one cDNA fragment containing the enzyme I site on only one end and the enzyme II site on the opposite end, wherein the enzyme II site is not cleavable by enzyme I and the enzyme I site is not cleavable by enzyme II;

(6) performing at least one polymerase chain reaction using the cDNA fragments obtained in step (5) as a substrate and using a first primer containing the enzyme I site and a second primer containing the enzyme II site;

(7) inserting the cDNA fragments amplified in step (6) that contain the enzyme I site on only one end and the enzyme II site on the opposite end into a eucaryotic cell expression vector containing a reporter gene to generate cDNA-reporter gene expression vectors, wherein the reporter gene contains a DNA sequence coding for a secretory protein lacking the signal peptide and wherein the cDNA fragments are inserted upstream of the reporter gene; and (8) transforming the cDNA-reporter gene expression vectors obtained in step (7) into a host cell capable of replicating the eucaryotic cell expression vector.

2. A process according to claim 1, wherein step (7) further comprises:

digesting the cDNA fragments amplified in step 6 with enzyme I and enzyme II and then inserting the digested cDNA fragments into the eucaryotic cell expression vector, wherein the vector is linear and contains ends capable of ligating to only those digested fragments that contain a cleaved enzyme I site on one end and a cleaved enzyme II site on the opposite end.

3. A process according to claim 1, wherein the enzyme I is EcoRI, the enzyme II is SacI, and the reporter gene codes for a human IL-2α receptor lacking the signal peptide.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1797 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: CDS
        ( B ) LOCATION: 82..351

( i x ) FEATURE:
        ( A ) NAME/KEY: sig_peptide
        ( B ) LOCATION: 82..138

( i x ) FEATURE:
        ( A ) NAME/KEY: mat_peptide
        ( B ) LOCATION: 139..348

( x i ) SEQUENCE DESCRIPTION: SEQ ID NO:1:

```
GACCACTTTC  CCTCTCGGTC  CACCTCGGTG  TCCTCTTGCT  GTCCAGCTCT  GCAGCCTCCG                60

GCGCGCCCTC  CCGCCCACGC  C ATG GAC GCC AAG GTC GTC GCC GTG CTG GCC                    111
              Met Asp Ala Lys Val Val Ala Val Leu Ala
              -19              -15                 -10

CTG GTG CTG GCC GCG CTG TGC ATC AGT GAC GGT AAA CCA GTC AGC CTG                      159
Leu Val Leu Ala Ala Leu Cys Ile Ser Asp Gly Lys Pro Val Ser Leu
              -5                  1                   5

AGC TAC CGA TGC CCC TGC CGG TTC TTC GAG AGC CAC ATC GCC AGA GCC                      207
Ser Tyr Arg Cys Pro Cys Arg Phe Phe Glu Ser His Ile Ala Arg Ala
         10              15                  20

AAC GTC AAG CAT CTG AAA ATC CTC AAC ACT CCA AAC TGT GCC CTT CAG                      255
Asn Val Lys His Leu Lys Ile Leu Asn Thr Pro Asn Cys Ala Leu Gln
     25                  30                  35

ATT GTT GCA CGG CTG AAG AAC AAC AAC AGA CAA GTG TGC ATT GAC CCG                      303
Ile Val Ala Arg Leu Lys Asn Asn Asn Arg Gln Val Cys Ile Asp Pro
 40                  45                  50                  55
```

```
AAA TTA AAG TGG ATC CAA GAG TAC CTG GAG AAA GCT TTA AAC AAG TAAGCACAA  358
Lys Leu Lys Trp Ile Gln Glu Tyr Leu Glu Lys Ala Leu Asn Lys
             60                      65                  70

AGCCCAAAGG ACTTTCCAGT AGACCCCCGA GGAAGGCTGA CATCCGTGGG AGATGCAAGG   418
GCAGTGGTGG GGAGGAGGGC CTGAACCCTG GCCAGGATGG CCGGCGGGAC AGCACTGACT   478
GGGGTCATGC TAAGGTTTGC CAGCATAAAG ACACTCCGCC ATAGCATATG GTACGATATT   538
GCAGCTTATA TTCATCCCTG CCCTCGCCCG TGCACAATGG AGCTTTATA  ACTGGGGTTT   598
TTCTAAGGAA TTGTATTACC CTAACCAGTT AGCTTCATCC CCATTCTCCT CATCCTCATC   658
TTCATTTTAA AAAGCAGTGA TTACTTCAAG GGCTGTATTC AGTTTGCTTT GGAGCTTCTC   718
TTTGCCCTGG GGCCTCTGGG CACAGTTATA GACGGTGGCT TTGCAGGGAG CCCTAGAGAG   778
AAACCTTCCA CCAGAGCAGA GTCCGAGGAA CGCTGCAGGG CTTGTCCTGC AGGGGGCGCT   838
CCTCGACAGA TGCCTTGTCC TGAGTCAACA CAAGATCCGG CAGAGGGAGG CTCCTTTATC   898
CAGTTCAGTG CCAGGGTCGG GAAGCTTCCT TTAGAAGTGA TCCCTGAAGC TGTGCTCAGA   958
GACCCTTTCC TAGCCGTTCC TGCTCTCTGC TTGCCTCCAA ACGCATGCTT CATCTGACTT  1018
CCGCTTCTCA CCTCTGTAGC CTGACGGACC AATGCTGCAA TGGAAGGGAG GAGAGTGATG  1078
TGGGGTGCCC CCTCCCTCTC TTCCCTTTGC TTTCCTCTCA CTTGGGCCCT TTGTGAGATT  1138
TTTCTTTGGC CTCCTGTAGA ATGGAGCCAG ACCATCCTGG ATAATGTGAG AACATGCCTA  1198
GATTTACCCA CAAAACACAA GTCTGAGAAT TAATCATAAA CGGAAGTTTA AATGAGGATT  1258
TGGACCTTGG TAATTGTCCC TGAGTCCTAT ATATTTCAAC AGTGGCTCTA TGGGCTCTGA  1318
TCGAATATCA GTGATGAAAA TAATAATAAT AATAATAATA ACGAATAAGC CAGAATCTTG  1378
CCATGAAGCC ACAGTGGGGA TTCTGGGTTC CAATCAGAAA TGGAGACAAG ATAAAACTTG  1438
CATACATTCT TATGATCACA GACGGCCCTG GTGGTTTTTG GTAACTATTT ACAAGGCATT  1498
TTTTTACATA TATTTTGTG  CACTTTTTAT GTTTCTTTGG AAGACAAATG TATTTCAGAA  1558
TATATTTGTA GTCAATTCAT ATATTTGAAG TGGAGCCATA GTAATGCCAG TAGATATCTC  1618
TATGATCTTG AGCTACTGGC AACTTGTAAA GAAATATATA TGACATATAA ATGTATTGTA  1678
GCTTCCGGT  GTCAGCCACG GTGTATTTTT CCACTTGAAA TGAAATTGTA TCAACTGTGA  1738
CATTATATGC ACTAGCAATA AAATGCTAAT TGTTTCATGC TGTAAAAAAA AAAAAAAA    1797
```

(2) INFORMATION FOR SEQ ID NO:2:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Ala Lys Val Val Ala Val Leu Ala Leu Val Leu Ala Ala Leu
-19             -15                 -10                 -5

Cys Ile Ser Asp Gly Lys Pro Val Ser Leu Ser Tyr Arg Cys Pro Cys
              1                 5                  10

Arg Phe Phe Glu Ser His Ile Ala Arg Ala Asn Val Lys His Leu Lys
         15                  20                 25

Ile Leu Asn Thr Pro Asn Cys Ala Leu Gln Ile Val Ala Arg Leu Lys
 30                 35                  40                  45

Asn Asn Asn Arg Gln Val Cys Ile Asp Pro Lys Leu Lys Trp Ile Gln
              50                  55                  60
```

|     | Glu | Tyr | Leu | Glu | Lys | Ala | Leu | Asn | Lys |
|-----|-----|-----|-----|-----|-----|-----|-----|-----|-----|
|     |     |     |     | 65  |     |     |     |     | 70  |

( 2 ) INFORMATION FOR SEQ ID NO:3:

( i ) SEQUENCE CHARACTERISTICS:
        ( A ) LENGTH: 1797 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:3:

```
GACCACTTTC CCTCTCGGTC CACCTCGGTG TCCTCTTGCT GTCCAGCTCT GCAGCCTCCG      60
GCGCGCCCTC CCGCCCACGC CATGGACGCC AAGGTCGTCG CCGTGCTGGC CCTGGTGCTG     120
GCCGCGCTCT GCATCAGTGA CGGTAAACCA GTCAGCCTGA GCTACCGATG CCCCTGCCGG     180
TTCTTCGAGA GCCACATCGC CAGAGCCAAC GTCAAGCATC TGAAAATCCT CAACACTCCA     240
AACTGTGCCC TTCAGATTGT TGCACGGCTG AAGAACAACA ACAGACAAGT GTGCATTGAC     300
CCGAAATTAA AGTGGATCCA AGAGTACCTG GAGAAAGCTT TAAACAAGTA AGCACAACAG     360
CCCAAAGGAC TTTCCAGTAG ACCCCCGAGG AAGGCTGACA TCCGTGGGAG ATGCAAGGGC     420
AGTGGTGGGG AGGAGGGCCT GAACCCTGGC CAGGATGGCC GGCGGGACAG CACTGACTGG     480
GGTCATGCTA AGGTTTGCCA GCATAAAGAC ACTCCGCCAT AGCATATGGT ACGATATTGC     540
AGCTTATATT CATCCCTGCC CTCGCCCGTG CACAATGGAG CTTTTATAAC TGGGGTTTTT     600
CTAAGGAATT GTATTACCCT AACCAGTTAG CTTCATCCCC ATTCTCCTCA TCCTCATCTT     660
CATTTTAAAA AGCAGTGATT ACTTCAAGGG CTGTATTCAG TTTGCTTTGG AGCTTCTCTT     720
TGCCCTGGGG CCTCTGGGCA CAGTTATAGA CGGTGGCTTT GCAGGGAGCC CTAGAGAGAA     780
ACCTTCCACC AGAGCAGAGT CCGAGGAACG CTGCAGGGCT TGTCCTGCAG GGGGCGCTCC     840
TCGACAGATG CCTTGTCCTG AGTCAACACA AGATCCGGCA GAGGGAGGCT CCTTTATCCA     900
GTTCAGTGCC AGGGTCGGGA AGCTTCCTTT AGAAGTGATC CCTGAAGCTG TGCTCAGAGA     960
CCCTTTCCTA GCCGTTCCTG CTCTCTGCTT GCCTCCAAAC GCATGCTTCA TCTGACTTCC    1020
GCTTCTCACC TCTGTAGCCT GACGGACCAA TGCTGCAATG GAAGGGAGGA GAGTGATGTG    1080
GGGTGCCCCC TCCCTCTCTT CCCTTTGCTT TCCTCTCACT TGGGCCCTTT GTGATATTTT    1140
TCTTTGGCCT CCTGTAGAAT GGAGCCAGAC CATCCTGGAT AATGTGAGAA CATGCCTAGA    1200
TTTACCCACA AAACACAAGT CTGAGAATTA ATCATAAACG GAAGTTTAAA TGAGGATTTG    1260
GACCTTGGTA ATTGTCCCTG AGTCCTATAT ATTTCAACAG TGGCTCTATG GGCTCTGATC    1320
GAATATCAGT GATGAAAATA ATAATAATAA TAATAATAAC GAATAAGCCA GAATCTTGCC    1380
ATGAAGCCAC AGTGGGGATT CTGGGTTCCA ATCAGAAATG GAGACAAGAT AAAACTTGCA    1440
TACATTCTTA TGATCACAGA CGGCCCTGGT GGTTTTGGT AACTATTTAC AAGGCATTTT     1500
TTTACATATA TTTTTGTGCA CTTTTATGT TCTTTGGAA GACAAATGTA TTTCAGAATA      1560
TATTTGTAGT CAATTCATAT ATTTGAAGTG GAGCCATAGT AATGCCAGTA GATATCTCTA    1620
TGATCTTGAG CTACTGGCAA CTTGTAAAGA AATATATATG ACATATAAAT GTATTGTAGC    1680
TTTCCGGTGT CAGCCACGGT GTATTTTCC ACTTGGAATG AAATTGTATC AACTGTGACA     1740
TTATATGCAC TAGCAATAAA ATGCTAATTG TTTCATGCTG TAAAAAAAAA AAAAAAA       1797
```

( 2 ) INFORMATION FOR SEQ ID NO:4:

( i ) SEQUENCE CHARACTERISTICS:

(A) LENGTH: 32 base pairs
(B) TYPE: nucleic acid
(C) STRANDEDNESS: single
(D) TOPOLOGY: linear (i i) MOLECULE TYPE: cDNA to mRNA (x i) SEQUENCE DESCRIPTION: SEQ ID NO:4:

GGAGATATCG AGCTCAATGG TGGCTGGGGA TG 32

(2) INFORMATION FOR SEQ ID NO:5:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: cDNA to mRNA (x i) SEQUENCE DESCRIPTION: SEQ ID NO:5:

GATGCGGCCG CCTCGAGGAA TTC 23

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: cDNA to mRNA (x i) SEQUENCE DESCRIPTION: SEQ ID NO:6:

GAGGTACAAG CTTGATATCG AGCTCGCGGC 30

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA to mRNA (x i) SEQUENCE DESCRIPTION: SEQ ID NO:7:

TTTACTTCTA GGCCTGTACG 20

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA to mRNA (x i) SEQUENCE DESCRIPTION: SEQ ID NO:8:

CCATGGCTTT GAATGTGGCG 20

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: single
(D) TOPOLOGY: linear ( i i ) MOLECULE TYPE: cDNA to mRNA ( x i ) SEQUENCE DESCRIPTION: SEQ ID NO:9:

GGAGATATCG AGCTCCTCGG GGTGGCACAG 30

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:10:

CCGCGAGCTC GATATCAAGC TTGTAC 26

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: modified_base
        ( B ) LOCATION: 1..23
        ( D ) OTHER INFORMATION: /note="A 17 mer dA ligated to a restriction enzyme site containing EcoRI (the 3' end)."

( x i ) SEQUENCE DESCRIPTION: SEQ ID NO:11:

GATGCGGCCG CCTCGAGGAA TCC 23